(12) United States Patent
Dubow

(10) Patent No.: US 7,897,642 B1
(45) Date of Patent: Mar. 1, 2011

(54) COMPOSITIONS AND METHODS FOR DRY EYE SYNDROME

(75) Inventor: Irvine Dubow, Naples, FL (US)

(73) Assignee: Dr. Irvine Dubow, St. Cloud, MN (US)

( * ) Notice: Subject to any disclaimer, the term of this patent is extended or adjusted under 35 U.S.C. 154(b) by 1834 days.

(21) Appl. No.: 10/464,105

(22) Filed: Jun. 18, 2003

Related U.S. Application Data

(60) Provisional application No. 60/389,671, filed on Jun. 19, 2002.

(51) Int. Cl.
*A61K 31/225* (2006.01)
*A61K 47/30* (2006.01)

(52) U.S. Cl. .................. 514/547; 514/772.3; 514/912

(58) Field of Classification Search ............ 514/547, 514/912, 772.3; 424/78.04
See application file for complete search history.

(56) References Cited

U.S. PATENT DOCUMENTS

| | | | | |
|---|---|---|---|---|
| 5,496,811 | A * | 3/1996 | Aviv et al. ............... | 514/78 |
| 6,620,797 | B2 * | 9/2003 | Chowhan et al. ......... | 514/57 |

* cited by examiner

*Primary Examiner* — Zohreh A Fay
(74) *Attorney, Agent, or Firm* — Schwegman, Lundberg & Woessner, P.A.

(57) ABSTRACT

Compositions and methods to inhibit dry eye as well as other conditions are provided.

21 Claims, No Drawings

COMPOSITIONS AND METHODS FOR DRY EYE SYNDROME

CROSS-REFERENCE TO RELATED APPLICATIONS

This application claims the benefit of the filing date of U.S. application Ser. No. 60/389,671, filed on Jun. 19, 2002, the disclosure of which is incorporated by reference herein.

BACKGROUND OF THE INVENTION

Traditional dry eye solutions, i.e., those for topical instillation of lubricating and wetting eye drops, contain tear substitutes. Tear substitutes or "artificial tears" attempt to emulate the composition and pH of normal tears and are intended to improve the continuous film and wetting over the corneal epithelial layer. For efficacy, the solutions often times may require instillation ten (10) times in a sixteen (16) hour day.

Traditional dry eye solutions consist of an isotonic or hypotonic aqueous solution of crystalloids, usually electrolytes of low molecular weight, carbohydrates and synthetic polymers, as well as preservatives. Synthetic polymers were generally added to dry eye solutions to increase the viscosity and retention time of the solution on the surface of the eye. However, increased viscosity interferes with lubrication. Further, an excess amount of the synthetic polymer decreases vision acuity. Many dry eye solutions also contain a preservative with bacteriostatic or bacteriocidal properties to extend the shelf life of the solution. Unfortunately, the preservative often causes allergic reactions, some of which are severe. To address this problem, some artificial tears are packaged singly and without a preservative. Nevertheless, allergic reactions may also be caused by other molecules in the solution, e.g., by pathogens or other immunogenic molecules in the solvent for dry eye solutions, i.e., water. Moreover, some traditional dry eye solutions combine indiscriminately cations and anions as well as non-ionic agents, which renders the resulting solutions electrostatically incompatible. See, e.g., U.S. Pat. No. 4,371,522; U.S. Pat. No. 4,775,531; U.S. Pat. No. 4,914,088, Glonet et al., 1995; JP Application 784147 and U.S. Pat. No. 6,428,453.

Thus, what is needed is an improved composition to treat dry eyes.

SUMMARY

The present approach does not follow the reductionist paradigm, nor does it focus on a specific effect, such as adjusting tonicity, enhancing lubrication by augmenting and maintaining a stable tear film over the ocular surface, adding a positively or negatively charged complex of phospholipids to the ocular surface of the eye, maintaining mucin goblet cells, and the like. Instead, the present subject matter provides compositions, e.g., pharmaceutical compositions, useful in a variety of applications, wherein the components of the composition are primarily non-ionic and suitable in compositions with other components, e.g., drugs or other bioactive molecules. As used herein, a "primarily non-ionic" composition includes a composition where a majority of the components in the composition are non-ionic. In one embodiment, the composition comprises a plurality of components, the majority of which are non-ionic in nature, which results in a particularly biocompatible composition.

In one embodiment, the composition is useful to relieve eye symptoms of patients such as patients with keratoconjunctivitis sicca. For example, a composition of the invention is introduced to the ophthalmic surface of the cornea and adnexia of a patient with dry eye syndrome, e.g., a composition formulated to return the eyes and its adnexia back to their normal electrostatic adjuvant state. The solution may be used as a spray or instilled as drops. Instead of frequent instillation, the composition may be administered only once or twice a day, or as often as needed, and yet reduce or inhibit symptoms of dry eye without harmful effects. Moreover, due to the non-ionic nature of the composition, there is no allergic reaction. In one embodiment, the ophthalmic composition comprises at least one surfactant, a component which destroys pathogens, e.g., bacteria, viruses, yeast, spores, molds, and fungi, preferably a preservative with reduced immunogenicity relative to thimerosol, a complexing agent, e.g., one which chelates metals, and deionized, demineralized, ozonated water.

In one embodiment, at least one surfactant is non-ionic. In one embodiment, at least one surfactant is present in the composition at about 0.001% to about 3.0%, e.g., about 0.01% to about 1% or about 0.02% to about 0.7%. In one embodiment, at least one surfactant is tyloxapol.

In one embodiment, the complexing agent is non-ionic. In another embodiment, the complexing agent is ionic. In one embodiment, a preferred complexing agent is EDTA. The complexing agent may be present in the composition at about 0.001% to about 3.0%, e.g., about 0.01% to about 1.0%, or about 0.02% to about 0.7%, by weight.

In one embodiment, the preservative is non-ionic. In one embodiment, the preservative may be present in the composition of about 0.01% to about 3%, e.g., about 0.1% to about 2%, by weight. In one embodiment, the preservative is parabens.

In one embodiment, the composition further comprises a fatty acid humectant. One example of a fatty acid humectant is glycerin. The fatty acid humectant is present in the composition at about 0.01% to about 3%, e.g., about 0.05% to about 2%, or 0.5% to about 1.0% by weight. The composition may further comprise a second surfactant, e.g., Tween 80. The second surfactant is present in the composition at about 0.01% to about 3%, e.g., about 0.05% to about 1% or 0.1% to about 0.5%.

The present subject matter also provides a method of preparing a composition of the invention. The method includes combining a preservative with reduced immunogenicity relative to thimerosol, a complexing agent, at least one surfactant, and deionized, demineralized, ozonated water. In one embodiment, tyloxapol, parabens and EDTA are combined. In another embodiment, tyloxapol, parabens, EDTA, glycerin and Tween 80 are combined.

Further provided is a method to inhibit or treat dry eye syndrome. The method includes contacting an ophthalmic surface with an effective amount of a composition of the invention. In one embodiment, a composition comprises tyloxapol, parabens and EDTA and optionally a fatty acid humectant and a surfactant which is not tyloxapol.

The composition of some embodiments of the present invention may also be employed in compositions and methods to inhibit or treat other conditions, e.g., to inhibit or treat fungal infections, e.g., of the nails or skin (epidermis), as well as to improve compositions that are intended to come into contact with the skin, such as a shaving solution, or to improve cleaning solutions or products. For example, the composition of the invention can result in a shaving product that permits a smoother, closer and more comfortable shave and extends the life of razor blades. Further, the composition of one embodiment of the invention can result in a cleaning solution that, once applied, is less apt to attract dust due to its non-ionic nature.

This Summary is an overview of some of the teachings of the present application and not intended to be an exclusive or exhaustive treatment of the present subject matter. Further details about the present subject matter are found in the detailed description and appended claims. Other aspects of the invention will be apparent to persons skilled in the art upon reading and understanding the following detailed description and viewing the drawings that form a part thereof, each of which are not to be taken in a limiting sense. The scope of the present invention is defined by the appended claims and their equivalents.

DETAILED DESCRIPTION

In the following detailed description, reference is made to the accompanying drawings which form a part hereof, and in which is shown by way of illustration specific embodiments in which the invention may be practiced. These embodiments are described in sufficient detail to enable those skilled in the art to practice the invention, and it is to be understood that the embodiments may be combined, or that other embodiments may be utilized and that chemical, structural, logical and electrical changes may be made without departing from the spirit and scope of the present invention. The following detailed description provides examples, and the scope of the present invention is defined by the appended claims and their legal equivalents.

It should be noted that references to "an", "one", or "various" embodiments in this disclosure are not necessarily to the same embodiment, and such references contemplate more than one embodiment.

The composition of certain embodiments of the present invention is useful to inhibit or treat dry eye, for instance, dry eye syndrome, blepharitis, ulcerative keratitis, microcysts, microbial keratitis, conjunctivitis, hypoxia, epithelial oedema, corneal desquamation, corneal infiltrates, giant papillary conjunctivitis, keratoconjunctivitis sicca, Sjogren's syndrome and other epithelial conditions of the cornea and its adnexa, to inhibit or treat conditions of the mucous membranes of the nasal passages, oral passages and bronchi, and in other compositions due to the low immunogenicity and/or non-ionic properties of the composition, e.g., in compositions to inhibit or treat nail fungus, shaving solutions, and cleaning solutions. "Dry eye syndrome" includes one or more of the following ocular symptoms: a sandy sensation, a gritty sensation, blurriness, discomfort, foreign body sensation, burning, dryness, persistent irritation, photophobia, poor lipid dispersion with accompanying dry spots, a spotty lipid layer, and the like. There are two general categories of dry eye syndrome; one where tear secretion is insufficient (less than normal), and another where tear secretion is normal. Keratoconjunctivitius sicca (KCS) caused by Sjogren's syndrome is characterized by insufficient tear secretion and dry mouth but no definable systemic disease. Secondary Sjogren's syndrome is where there is definable systemic disease, e.g., autoimmune diseases such as rheumatoid arthritis, lupus or scleroderma. Other causes of KCS include graft versus host disease, AIDS and lymphoma involving the lacrimal glands.

The tear film has three layers. The very thin outer layer contains lipids secreted by the meibomian glands located in the lid margins and behind the eyelashes. With each blink, the oil in the glands is expressed onto the outer surface of the tear film. The primary purpose of the outer layer is to prevent evaporation of the aqueous layer of the tear film, but it also acts as a barrier to foreign body particulates. The middle (thickest) layer is the aqueous layer is secreted by the main accessory lacrimal glands. The middle layer keeps the salinity and acidity of the tears at proper levels and contains many substances the eye needs to maintain surface health and prevent infection, such as antibodies and other immune defense agents. The innermost layer is the mucin layer that is secreted by the goblet cell located on the surface of the eye. The mucin layer serves a dual purpose; it provides a protective coating for the ocular surface and is also the agent by which the aqueous layer adheres to the cornea.

An inadequate or abnormal lipid layer will, of necessity, result in an inadvertent evaporation of the aqueous tear layer, thus leaving the ocular surface susceptible to charged environmental pollutants such as dirt, dust, sand, and soilage.

Non-systemic dry eye syndrome may be caused by one or more biological or environmental factors. Those factors include the lack of oily lipid secretion, an abnormality of the oily lipid layer yielding poor and inadequate coverage of the aqueous layer, an increased osmolarity due to the decreased tear production or increased tear production, lacrimal gland disease, dysfunction of the meibomian gland, which prevents sufficient tears to stop the overflow over the edge of the lower lid, meibomitis (an infection or inflammation of the meibomian glands), a problem with the innermost mucin layer, causing a decrease in goblet cells which are vital to allow the tear film to remain on the hydrophobic epithelial layer on the surface of the cornea, stroke, close work, e.g., reading, writing, computer, side effects of certain medications, such as antibiotics, antihistamines, diuretics or anti-diuretics, hormonal changes, air conditioning, wind, dirt, dust, sand, snow, smoke, pollen, or other allergens, contact lens use, aging of the tear glands, refractive surgery, neurotrophic keratitis due to decreased corneal sensitivity or long-term contact lens wear, idiopathic and the like. The most common causes of non-systemic dry eye syndrome are the lack of oily lipid secretion, an abnormality of the oily lipid layer yielding poor and inadequate coverage of the aqueous layer, or both. Ophthalmic disorders may be detected by, for example, osmolarity measurement, dilation of the ocular surface, capillaries, arterioles and angiomas, Schirmer's test, fluorescein break-up-time, Rose Bengal staining, Lisamine Green or biomicroscope.

Such embodiments of the present subject matter disrupt the cycle of dry eyes by interrupting or breaking the cycle that causes the problem(s) and returns the ocular surface and adnexia to a normal electrostatic state. Thus, the present compositions primarily include non-ionic components, as well as any and all other substances with balancing negative and positive charged ions, so that the components in the composition complement one another. A primarily non-ionic composition comprises less than about 50% w/v or v/v, e.g., less than 10%, 1% or 0.01% w/v or v/v, of ionic components. Moreover, in one embodiment, a primarily non-ionic composition is substantially free of immunogenic agents, e.g., pathogens, which avoids the stimulation of an allergic cascade, i.e., avoids mast cell involvement and mast cell or basophil degranulation, which are major factors in the inflammatory cascade. A composition which is "substantially free" of immunogenic agents includes a composition that does not elicit an immune response or elicits an immune response that is reduced, e.g., by at least 2-fold, 10-fold or reduced by even more, relative to the immune response to one or more immunogenic agents, e.g., a pathogen, as measured by hematopoietic cell-based assays.

All allergic reactions are the result of the mobilization of the immune system in response to a foreign substance in the body. The invention is formulated to have antibodies accept the solution as friendly and non-threatening, thus avoiding an allergic cascade, even though antibodies are important as a line of defense to protect the system from harmful invading parasites, foreign bodies or pollens, and to avoid a hypersensitivity response to the eye characterized by itching, redness, tearing, foreign body sensation and decreased vision.

The process of an allergic reaction is the provocation by a specific type of antibody. Immunoglobulins, including IgE, are made by B-lymphocytes (a specific white blood cell). The B-lymphocytes antibody production is regulated/overseen by helper lymphocytes (another type of white blood cell). Macrophages (a phagocytic tissue cell), which function to protect the body against infection and noxious substances, prompt B-lymphocytes to make more IgE.

Mast cells are large cells that are comprised of basophil granules containing substances such as histamines, cytokines, and the like, which mediate allergic reactions that act on mucous glands, inflammatory cells, connective tissues, etc. Mast cells reside in the tissues of the body and basophils are in the blood stream. They both have many specific IgE antibody receptors. When the allergen (antigen) is confronted, the antigen binds to these IgE receptors on the surface of the cornea (tear film). When the IgE antibodies, next to each other, bind to the antigen, which wiggles the phospholipids membrane and causes the mast cells or basophils to degranulate, this prompts the latter to release chemicals that cause an allergic reaction.

A mast cell phospholipid membrane is composed primarily of phospholipids, carbohydrates and proteins with the phospholipids molecules arranged in parallel rows (bilayer) that consist of a polar phosphate head which is hydrophilic (water loving) facing outward and a non-polar fatty acid tail that is hydrophobic (water hating) facing inward. The membrane is the gatekeeper and acts as a barrier to control the ingress and egress into and out of the cell and organelles. There are 10 main types of lipids in cell membranes. Each type of cell or organelle generally has a differing percentage of each lipid, protein, and carbohydrate.

The membrane is relatively permeable which means some things can pass through the membrane via osmosis or diffusion. The rate of diffusion will vary depending on its: size, polarity, charge and concentration on the inside of the membrane versus the concentration on the outside of the membrane. The membrane is relatively permeable to small non-ionic molecules, particularly if they are lipid soluble and may move freely through the membrane. Macromolecules and charged ions/molecules cannot move freely through the membrane. The outside layer is positively charged and the inside layer is negatively charged. Thus, the negatively charged ions move out of the mast cells and positively charged ions move in. The permeability of the cell membrane to a molecule depends on the size of the molecule, its solubility in lipid, its ionic charge and the presence of carrier molecules.

Normal movement across the membrane is essential for nutrition and removal of waste materials. The phospholipid membrane regulates the transfer of material between the cell and its environment, it gauges the concentration gradient of adenosine triphosphate (ATP), the energy currency of the cell, and transfers the energy by varying modes: intracellular, trancellular, facilitated or passive and active transport. The lipid layer is a major barrier to a vast number of water soluble substances, e.g., proteins and carbohydrates. One role of proteins in cells is for the transport of molecules/ions into or out of cells. Other roles are in cell recognition enzyme catalysis, receptors, and in cell to cell communication. Carbohydrates repel negative particles due to their negative charge, act as receptors for hormones and other regulatory molecules, and form specific cell markers that enable like cells to attach, aggregate and enter into immune reactions.

The composition is non-ionic and the phospholipid membrane is permeable to small non-ionic molecules, thus the non-ionic molecules move freely. At first, the observation of like molecules repelling and unlike attracting, appears simple, but in fact, even though Van der Waal's forces are always present, so much depends on the charges held and under what conditions they move or whether they are at the surface or floating freely. Even though there is a motion of charges in bodies and they are electrically neutral, momentarily, at any given instant, on onset of charges may set up an electric field that reacts or disturbs to rearrange another set of charges. This changing of the electric fields that effect one another is called "Van der Waal's", "thermodynamics" or "charge fluctuation".

The formulation combines the chemical, biophysical with the biomolecular etc. It does not follow the reductionist paradigm but rather Hood's biological system. It includes intermolecular forces as, of inestimable, invaluable consideration, which may be referred to in this instance, as the Gestalt/coulomb approach, (which also includes Van der Waal forces, Debye-Huckel and London).

Coulomb's Law also known as the law of forces, is an embodiment of organic chemistry. Like Newton's Law of Gravity it too is in the same category and is scientifically fundamental. It applies to: trends in the periodic table, the relative stability of atoms and molecules, ionic vs covalent molecules, inter molecular interactions, physical properties of molecules and chemical reactivity.

According to Coulomb's law, like particles repel and unlike particles attract. The electrostatic force between two charged particles is directly proportional to the magnitude of the charge of each particle. This expansion indicates that opposite charges attract, leading to a more stable system. The converse: like charges repel and the repulsion also adds to a more stable system. This is a critical point that relates to the energy and potential energy in atoms and molecules.

Whereas Coulomb's law is relatively strong and has long range forces, the others do not. Van der Waal's forces/bonding and dispersion forces produce a temporary, fluctuating dipole action whereby the ions (electrons) are always in motion. They are the weakest of the forces, but are important because they are always present. They may be found one moment at one end of the molecule and almost instantaneously at the other end. There is constant movement of the molecules, inter and intra. This gives rise to dipole-intermolecular attraction and an instant later, both molecules reverse and in so doing will repel each other (chemguide.co.uk/atoms/bonding/vdw.html). Debye-Hunckel's Limiting law takes it one step further. This motion is not entirely random, as there is a slight tendency for the ions of the opposite charge to encounter each other frequently. The counter ions, (negative anions) have a net charge equal in magnitude but opposite in sign from the central positive cations. The atmosphere is thus ionic in nature.

The environment of the tear film lends itself greatly to this phenomenon. The aqueous component of the tear layer consists of water, electrolytes, glucose, urea, glycoproteins, primary tear proteins and serum proteins. Aqueous tears enable normal corneal metabolism since they provide the cornea with glucose, water and electrolytes. Furthermore, they provide for the elimination of carbon dioxide, lactic acid as well as flush away debris while providing lubrication of the ocular surface.

Exemplary Compositions

The composition of various embodiments of the present subject matter may be employed in ophthalmic compositions or non-ophthalmic compositions. The ophthalmic compositions may be employed for dry eye syndrome, blepharitis, conjunctivitis, e.g., giant papillary and the like, keratitis (ulcerative or microbial) or in anti-bacterial ophthalmic compositions, e.g., in compositions to treat Pseudomonas aeruginosa infection of the eye, or any condition of the cornea, lids, orbit, glands or adnexia. The non-ophthalmic compositions comprising one or more of the components described herein may be employed for fungal infections (local), e.g., fungal infection of toe nails or finger nails, or between fingers or toes (athletes foot), bacterial infections, vaginal yeast infections, in compositions for skin problems such as acne, or in compositions administered to the bronchi, nasal passages, sinuses or for airway clearance, or to relieve external itching and irritation. In one embodiment, all of the components of the composition are non-ionic, which makes the composition electrostatically quiescent biocompatible, and of low immunogenicity, i.e., which avoids or reduces inflammatory triggering mechanisms.

The composition specifically includes an aqueous vehicle that is free of an electronic charge, e.g., deionized/demineralized/non-ionized purified water. The deionized/demineralized/non-ionized purified water is subjected to ozonation to kill fungi, algae, yeast spores, microbacteria, viruses, molds and mildew, and to remove agents such as disrupted (non-intact) pathogens, prior to mixing with other substances.

For example, deionized/demineralized/non-ionic purified water is prepared by using plastic beds (exchange resins) and an advanced membrane separation technology that removes almost all the ionized mineral salts, including the salts that contribute to hardness and alkalinity. It will produce water quality that reduces 100 micro ohms to 10 micro ohms. However, as the quality of the water is very significant to the invention, the latter refers to dissolved solids only. Deionization alone does not improve or remove bacteria, viruses, fungi, microbacteria, molds, and yeast spores, etc.

One of the major benefits of ozonation is its ability to oxidize substances. While harmless, sanitary and innocuous (given Gras status by the FDA for bottled water in 1982 and generally recognized as safe in 1997), it also attenuates harmful microbes and microbial pathogen by products. The efficacy of the composition may be monitored and the degree of effectiveness controlled. For example, ozone is most potent upon first being generated. Its half-life is 45 minutes at 68° F., and in two hours its concentrated effectiveness is 16% of its initial value. It must be newly generated for immediate use in order to have the greatest lethal factor. The maximum dose is 5% ozone to 95% oxygen.

Moreover, ozonation works faster, i.e., over 3,000 times faster, than chlorine, and so is safer and more efficient and therefore a better disinfectant. Unlike chlorine, the original ozone molecule reverts back to harmless oxygen. All pathogens (algae, yeast spores, fungi, viruses, and other microorganisms) are attacked and their cell walls or outer membranes are ruptured. By reverting back to oxygen, ozone leaves no chemical residue. It is also highly reactive with synthetic products or their metabolites, as well as with their residue. It breaks down harmful chemicals and debris (such as dead microbes), which is very helpful in not triggering an inflammatory cascade. Equally important, after this action is performed, its efficacy can be controlled to the proper degree essential to perform the requisite task. In other words, the initial oxidation strength is modified as desired. Ozone can be created artificially as a result of ultraviolet light acting on oxygen, a hot spark or cold plasma.

Another component of the composition is a complexing agent, e.g., ethylene diamine tetraacetic acid trisodium salt (EDTA) or disodium edentate, EGTA, or the like that sequester (chelate) heavy metals such as copper, iron and nickel by catalyzing the oxidation of lipids to form tightly bound complexes. The polyvalent metal ions form a soluble metal complex, thus improving the quality and stability of the composition. This also assists the composition to disperse metal salts and impurities to prevent deposition in the solvent and/or what may be found in lacrimal tear film. For example, EDTA has an anionic charge and is very useful to complex a metal ion, e.g., a transition metal ion that has a central cation, and optionally an attached anion or neutral molecule present in solution (or the tear layer). Thus, EDTA is a complexing agent which needs electrons and forms a very stable complex with bonds to metal ions, e.g., toxic metal ions, i.e., it sequesters metals. In one embodiment, the complexing agent is present in the composition at about 0.001% to about 5.0%, e.g., about 0.01% to about 2.5%, about 0.1% to about 2.0% or about 0.5% to about 1.0% by weight.

Another component of the composition is a non-ionic surfactant, e.g., tyloxapol and Triton X-100. For example, tyloxapol is a non-ionic alkalaryl and polyester alcohol that reduces surface tension, inhibits microscopic lipid particles in the blood stream during fat digestion and assimilation (chylomicron), and has anti-inflammatory, anti-oxidant, and mucoactive properties. In one embodiment, the surfactant is present in the composition at about 0.001% to about 3%, e.g., about 0.05% to about 2% or about 0.1% to about 2%, about 0.01% to about 1.0% by weight.

The composition also comprises a preservative that has reduced immunogenicity relative to thimersol. For example, parabens (methyl, propyl, ethyl and the like) is a non-ionic preservative that extends the shelf life of the composition and is very effective against yeasts and molds. In one embodiment, both methyl and propyl parabens are used in the composition, with two to three parts of methyl paraben with one part of propyl paraben. The preservative is present in the composition at about 0.01% to about 2.5%, e.g., such as about 0.5% by weight.

Other preservatives include those having the structure (I):

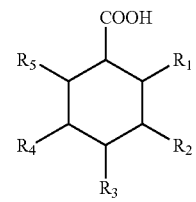

wherein $R_1$, $R_2$, $R_4$, and $R_5$ are independently selected from the group consisting of H, OH, F, I, Br, Cl, SH, $NH_2$, CN, alkyl, alkoxyl, $NR_2$, OR, $NO_2$, COR, $CONR_2$, $CO_2R$, $SO_3R$; wherein R is independently selected from the group consisting of H, alkyl, and alkoxyl groups. $R_3$ is independently selected from the group consisting H, OH, F, I, Br, Cl, SH, CN, alkyl, alkoxyl, OR, $NO_2$, COR, $CONR_2$, $CO_2R$, $SO_3R$; wherein R is independently selected from the group consisting H, alkyl, and alkoxyl groups.

Suitable alkyl groups include saturated or unsaturated, linear or branched chain, substituted or unsubstituted alkyl groups, preferably $C_1$-$C_4$, more preferably $C_1$-$C_3$, most preferably $C_1$-$C_2$ alkyl groups (preferably $CH_3$ or $CH_2C$). Nonlimiting examples of substituted alkyls are $CH_2CO_2R$, $CH_2OR$, $CH_2OR$, $CH_2COR$, and $CH_2NR_2$, where R is defined as above.

Suitable alkoxyl groups include saturated or unsaturated, linear or branched chain, substituted or unsubstituted alkoxyl groups, preferably $C_1$-$C_1$, more preferably $C_1$-$C_3$, most preferably $C_1$-$C_2$ alkoxyl groups (preferably $CH_3$ or $CH_2C$).

Preferred halogens are selected from the group consisting of I, Br and Cl.

In one embodiment, the composition comprises a second non-ionic surfactant, e.g., polyoxyethylene sorbitan-mono-olleate (commercially, Tween 80), Tween 20, Tween 40, Tween 60 and Tween 85. Tween 80 promotes polymerization and acts as a wetting and penetrating agent. The second surfactant is present in the composition at about 0.001% to about 3%, e.g., about 0.05% to about 2%, or about 0.03% to about 1%, e.g., about 0.02%, by weight.

In one embodiment, the composition comprises a fatty acid humectant surfactant, e.g., glycerin and glyceride derivatives (e.g., mono, di, tri, glycerides), which are fats and oils that are esters of glycerol with one or more fatty acids. These agents promote retention of moisture to prevent dehydration, and thus are moistening agents and lubricants that are resistant to oxidation. In addition, the humectant is a good emulsifier and wetting agent. Other humectants may include a variety of these materials can be employed and each can be present at a level of from about 0.01% to about 20%, more preferably from about 0.1% to about 10%, e.g., 0.80% or about 0.5% to about 7% by weight of the composition.

In one embodiment, the composition comprises EDTA, e.g., 0.001% to 5.0% by weight, parabens, e.g., 0.5% by weight, 2-3:1 methyl paraben to propyl paraben, tyloxapol, e.g., 0.01 to 1.0% by weight, and optionally Tween 80, e.g., 0.02% by weight, and glycerine, e.g., 0.80% by weight.

All publications, patents and patent applications are incorporated herein by reference. While in the foregoing specification, this invention has been described in relation to certain preferred embodiments thereof, and many details have been set forth for purposes of illustration, it will be apparent to those skilled in the art that the invention is susceptible to additional embodiments and that certain of the details herein may be varied considerably without departing from the basic principles of the invention.

What is claimed is:

1. An ophthalmic composition comprising:
    two surfactants, one of which is tyloxapol;
    a preservative with reduced immunogenicity relative to thimerosol;
    a complexing agent; and
    deionized, demineralized, ozonated water.
2. The composition of claim 1 which is non-ionic.
3. The composition of claim 1 further comprising a fatty acid humectant.
4. The composition of claim 3 wherein the fatty acid humectant is glycerin.
5. The composition of claim 4 which comprises about 0.5% to about 1.0% by weight glycerin.
6. The composition of claim 1 wherein the second surfactant is Tween 80.
7. The composition of claim 6 which comprises about 0.05% to about 1.0% by weight Tween 80.
8. The composition of claim 1 wherein the preservative is parabens.
9. The composition of claim 8 which comprises about 0.1% to about 2% by weight paraben.
10. The composition of claim 1 wherein the complexing agent is EDTA.
11. The composition of claim 10 which comprises about 0.01% to about 1.0% by weight EDTA.
12. The composition of claim 1 which comprises about 0.01% to about 1.0% by weight tyloxapol.
13. The composition of claim 1 which is primarily non-ionic.
14. The composition of claim 1 which comprises tyloxapol, parabens and EDTA.
15. The composition of claim 1 which comprises tyloxapol, parabens, EDTA, glycerin and Tween 80.
16. A method of preparing an ophthalmic composition comprising combining a preservative with reduced immunogenicity relative to thimerosol, a complexing agent, at least two surfactants, one of which is tyloxapol, and deionized, demineralized, ozonated water.
17. The method of claim 16 in which tyloxapol, parabens and EDTA are combined.
18. A method to inhibit or treat non-systemic dry eye syndrome, comprising:
    contacting an ophthalmic surface with an effective amount of the composition of claim 1 or an ophthalmic composition comprising two surfactants, one of which is tyloxapol, parabens, a complexing agent, and deionized, demineralized, ozonated water.
19. The method of claim 18 wherein the composition comprises tyloxapol, parabens and EDTA.
20. An ophthalmic composition comprising two surfactants, one of which is tyloxapol, parabens, a complexing agent, and deionized, demineralized, ozonated water.
21. The composition of claim 1 or 20 which is aqueous.

* * * * *